United States Patent
Armato, III et al.

(10) Patent No.: US 6,577,752 B2
(45) Date of Patent: Jun. 10, 2003

(54) AUTOMATED METHOD AND SYSTEM FOR THE DELINEATION OF THE CHEST WALL IN COMPUTED TOMOGRAPHY SCANS FOR THE ASSESSMENT OF PLEURAL DISEASE

(75) Inventors: Samuel G. Armato, III, Downers Grove, IL (US); Heber MacMahon, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 20 days.

(21) Appl. No.: 09/881,002

(22) Filed: Jun. 15, 2001

(65) Prior Publication Data

US 2002/0191827 A1 Dec. 19, 2002

(51) Int. Cl.⁷ ................................................. G06K 9/00
(52) U.S. Cl. .......................... 382/131; 382/132; 382/169
(58) Field of Search ............................... 382/128, 129, 382/130, 131, 132, 195, 172, 199, 203, 173, 169; 600/407, 528, 531, 532, 533, 534, 535, 538; 604/304, 19, 20, 516, 509, 101.01, 101.04; 424/450, 1.69, 1.37, 1.65; 128/922; 378/37, 146; 250/363.02

(56) References Cited

U.S. PATENT DOCUMENTS

| | | | |
|---|---|---|---|
| 5,319,549 A | * 6/1994 | Katsuragawa et al. | 382/108 |
| 5,572,565 A | * 11/1996 | Abdel-Mottaleb | 378/37 |
| 5,638,458 A | * 6/1997 | Giger et al. | 382/132 |
| 5,850,465 A | * 12/1998 | Shimura et al. | 382/132 |
| 6,139,505 A | * 10/2000 | Murphy | 600/532 |
| 6,287,290 B1 | * 9/2001 | Perkins et al. | 604/516 |
| 6,483,934 B2 | * 11/2002 | Armato et al. | 382/132 |

* cited by examiner

Primary Examiner—Bhavesh M. Mehta
Assistant Examiner—Abolfazl Tabatabai
(74) Attorney, Agent, or Firm—Oblon, Spivak, McClelland, Maier & Neustadt, P.C.

(57) ABSTRACT

A method, system, and computer program product for automated measurements of pleural space and/or pleural thickening in thoracic CT images to identify the presence and quantify the extent of pleura-based disease, including obtaining a CT image including the pleural space and/or the pleural thickening, segmenting lungs in the obtained image, constructing a chest wall image from the obtained image using a lung boundary obtained in the segmenting step, identifying ribs in the chest wall image, mapping a location of the identified ribs back into the obtained image, and determining in the obtained image the extent of the pleural space and/or the pleural thickening between the identified ribs mapped back into the obtained CT image and at least one segmented lung. Exemplary embodiments include determining the extent of pleural space and/or pleural thickening based on linear distance, area, and volume of the space between the ribs and the lung boundary. These pleural determinations may be used to quantify the extent of disease in a particular case as additional information to be incorporated into a radiologist's decision-making process, or as part of a computer-aided diagnostic scheme that alerts radiologists of the potential for pleural disease in the case.

21 Claims, 16 Drawing Sheets

FIG. 3B
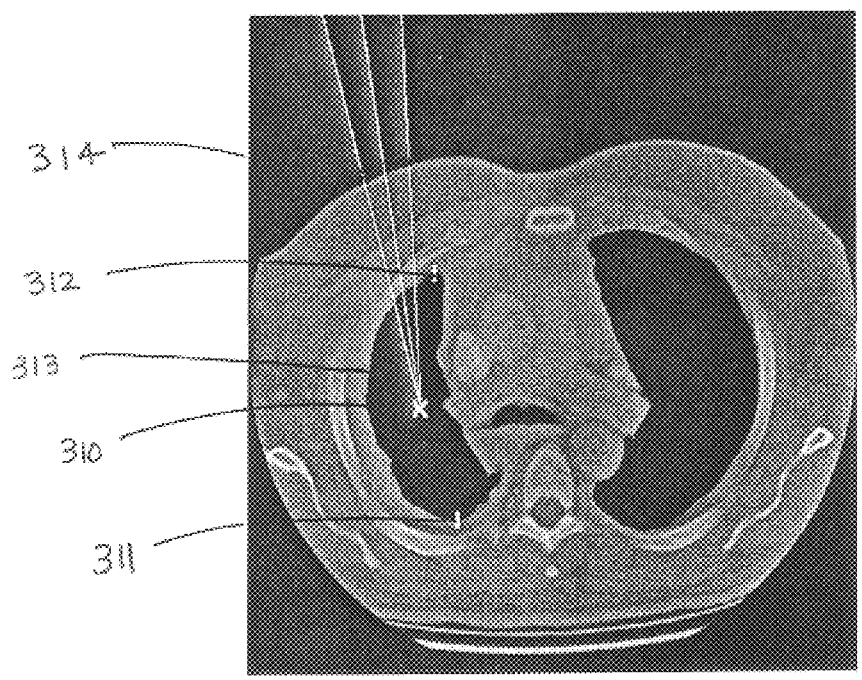
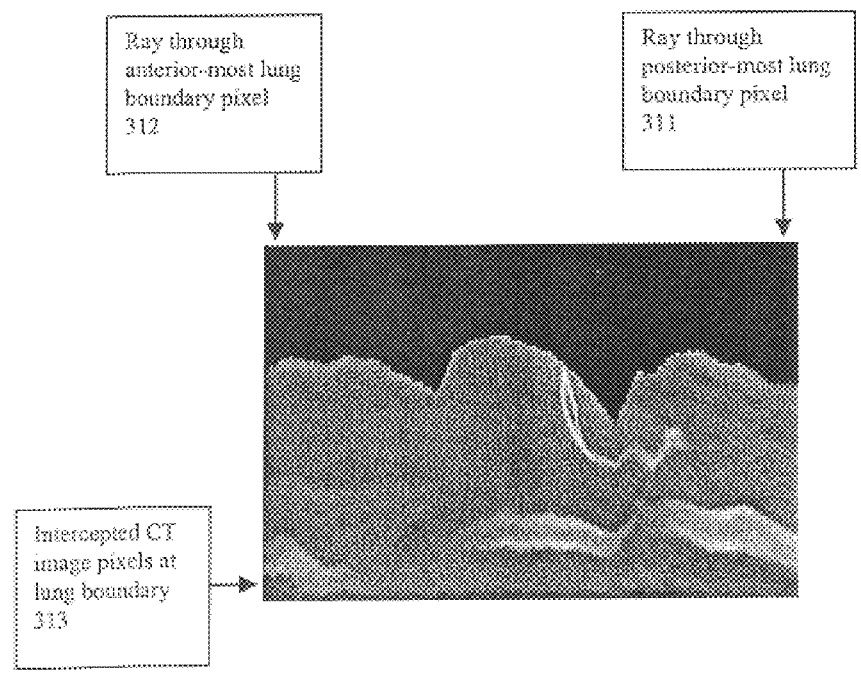
FIG. 3C

Original Image    Chest Wall Image lung centroid

| < Geometric parameters of RIGHT RIBS > <br> -- ordered from anterior to posterior -- | < Geometric parameters of LEFT RIBS > <br> -- ordered from anterior to posterior -- |
|---|---|
| Rib Xcent Ycent Area Pleural thickness <br> 1  139  197  217.0   6.6 mm <br> 2   78  316  465.0  13.5 mm <br> 3  143  408  756.5  11.8 mm | Rib Xcent Ycent Area Pleural thickness <br> 1  347  162  404.5  1.6 mm <br> 2  439  279  700.5  1.4 m <br> 3  365  407  662.0  5.1 mm |

FIG. 8

AUTOMATED METHOD AND SYSTEM FOR THE DELINEATION OF THE CHEST WALL IN COMPUTED TOMOGRAPHY SCANS FOR THE ASSESSMENT OF PLEURAL DISEASE

The present invention was made in part with U.S. Government support under grant number CA83908 from the USPHS. The U.S. Government may have certain rights to this invention.

BACKGROUND OF THE INVENTION

Field of the Invention

The invention relates generally to the computerized, automated assessment of computed tomography (CT) scans (or images), and more particularly, to methods, systems, and computer program products for delineating the chest wall in helical CT scans of the thorax to assess pleural disease.

The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,832,103; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,138,045; 6,141,437; 6,185,320; 6,205,348 as well as U.S. patent application Ser. Nos. 08/173,935; 08/398,307 (PCT Publication WO 96/27846); 08/536,149; 08/900,188; 08/900,189; 09/027,468; 09/028,518; 09/092,004; 09/121,719; 09/141,535; 09/471,088; 09/692,218; 09/716,335; 09/759,333; 09/760,854; 09/773,636; 09/816,217; 09/830,562; and 09/830,574 and PCT patent applications PCT/US00/41299; PCT/US01/00680; PCT/US01/01478 and PCT/US01/01479, all of which are incorporated herein by reference.

The present invention includes use of various technologies referenced and described in the above-noted U.S. patents and applications, as well as described in the references identified in the following LIST OF REFERENCES by the author(s) and year of publication and cross-referenced throughout the specification by reference to the respective number, in parentheses, of the reference:

LIST OF REFERENCES

1. Ng C S, Munden R F, Libshitz H I. Malignant pleural mesothelioma: The spectrum of manifestations on CT in 70 cases. *Clinical Radiology* 54:415–421, 1999.
2. Sterman D H, Kaiser L R, Albelda S M. Advances in the treatment of malignant pleural mesothelioma. *Chest* 116:504–520, 1999.
3. Huo Z, Giger M L, Vyborny C J, Bick U, Lu P, Wolverton D E, Schmidt R A. Analysis of spiculation in the computerized classification of mammographic masses. *Medical Physics* 22:1569–1579, 1995.
4. Jiang Y, Nishikawa R M, Wolverton D E, Metz C E, Giger M L, Schmidt R A, Vyborny C J, Doi K. Malignant and benign clustered microcalcifications: Automated feature analysis and classification. *Radiology* 201:581–582, 1996.
5. Giger M L, Doi K, MacMahon H, Nishikawa R M, Hoffmann K R, Vyborny C J, Schmidt R A, Jia H, Abe K, Chen X, Kano A, Katsuragawa S, Yin F -F, Alperin N, Metz C E, Behlen F M, Sluis D. An "intelligent" workstation for computer-aided diagnosis. *RadioGraphics* 13:647–656, 1993.
6. Xu X -W, Doi K, Kobayashi T, MacMahon H, Giger M L. Development of an improved CAD scheme for automated detection of lung nodules in digital chest images. *Medical Physics* 24:1395–1403, 1997.
7. Katsuragawa S, Doi K, MacMahon H, Monnier-Cholley L, Ishida T, Kobayashi T. Classification of normal and abnormal lungs with interstitial diseases by rule-based method and artificial neural networks. *Journal of Digital Imaging* 10:108–114, 1997.
8. Difazio M C, MacMahon H, Xu X -W, Tsai P, Shiraishi J, Armato S G, III, Doi K. Digital chest radiography: Effect of temporal subtraction images on detection accuracy. *Radiology* 202:447–452, 1997.
9. Armato S G, III, Giger M L, MacMahon H. Automated detection of lung nodules in CT scans: Preliminary results. *Medical Physics* (in press), 2001.
10. Webb W R, Brant W E, Helms C A. *Fundamentals of Body CT*. Philadelphia, Pa.: W. B. Saunders Company; 1998.
11. Giger M L, Bae K T, MacMahon H. Computerized detection of pulmonary nodules in computed tomography images. *Investigative Radiology* 29:459–465, 1994.
12. Sonka M, Hlavac V, Boyle R. *Image Processing, Analysis, and Machine Vision*. Pacific Grove, Calif.: Brooks/Cole Publishing Company; 1999.
13. Armato S G, III, Giger M L, Moran C J, Doi K, MacMahon H. Computerized detection of lung nodules in computed tomography scans. In: K Doi, H MacMahon, M L Giger, and K R Hoffmann, eds. *Computer-Aided Diagnosis in Medical Images*. Amsterdam: Elsevier Science; 1999:119–123.
14. Armato S G, III, Giger M L, Blackburn J T, Doi K, MacMahon H. Three-dimensional approach to lung nodule detection in helical CT. *SPIE Proceedings* 3661:553–559, 1999.
15. Armato S G, III, Giger M L, Moran C J, MacMahon H, Doi K. Automated detection of pulmonary nodules in helical computed tomography images of the thorax. *SPIE Proceedings* 3338:916–919, 1998.
16. Fitzgibbon A W, Pilu M, Fisher R B. Direct least squares fitting of ellipses. In: eds. *International Conference on Pattern Recognition*. Vienna: IEEE Computer Society; 1996.
17. Mathews J H. *Numerical Methods for Mathematics, Science, and Engineering*. Englewood Cliffs, N.J.: Prentice Hall; 1992.

DISCUSSION OF THE BACKGROUND

Malignant pleural mesothelioma is diagnosed in approximately 2000–3000 people in the Unites States each year (see Reference 1) and is associated with an extremely poor prognosis. Given the correlation of mesothelioma with asbestos exposure and a latency of up to 35–40 years (see Reference 1), the incidence of malignant mesothelioma is expected to rise over the next decade or two. Although numerous attempts to develop an accepted treatment for the management of mesothelioma patients have been largely unsuccessful, investigators continue to explore novel chemotherapy agents and multimodality treatment programs in an effort to reduce morbidity and, potentially, prolong the survival of patients afflicted with this disease (see Reference 2).

Computed tomography (CT) has been a major advance in the diagnosis and assessment of mesothelioma. Moreover, CT is an important tool for monitoring a patient's response to treatment in a variety of clinical trials. The increased use of CT in the evaluation of mesothelioma demands new, computerized image analysis methodologies to facilitate extraction of the image features that are most relevant to the characterization of mesothelioma. Image processing and computer vision techniques have been developed for the detection and classification of breast masses and microcalcifications on mammograms (see References 3–5), for the detection of lung nodules and interstitial disease on chest radiographs (see References 6, 7), for the enhanced visualization of temporal change on sequential chest radiographs (see Reference 8), and for the detection of lung nodules in thoracic CT scans (see Reference 9). The evaluation of mesothelioma could benefit from similar techniques that would assist radiologists and clinicians in the reliable, consistent, and reproducible quantification of mesothelioma.

While currently no standard exists for radiologic measurement of mesothelioma, one protocol indicates manual measurement of up to three areas of the pleural rind at each of three levels (i.e., three separate CT sections). To accomplish this task, a radiologist holds a ruler up to the CT film, makes the appropriate measurement, and uses a scale printed on the film to convert the measurement of the image into the real-world size of the measured structure. More accurate and global assessment of mesothelioma certainly requires the acquisition of many more than nine measurements (i.e., three measurements on each of three CT sections).

However, the amount of effort required to accomplish this task with the current manual procedure places a practical limit on the number of measurements that may be acquired.

SUMMARY OF THE INVENTION

Accordingly, an object of this invention is to provide an improved method, system, and computer program product for the automated measurements of pleural space and pleural thickening in thoracic CT scans, including automated segmentation of lungs in thoracic CT scans, automated construction of a "chest wall image" from thoracic CT scans, automated and semi-automated identification (segmentation) of ribs in thoracic CT scans, and automated delineation of the chest wall in thoracic CT scans.

These and other objects are achieved by way of a method, system, and computer program product constructed according to the present invention, wherein pleural disease (particularly mesothelioma, a pleura-based cancer) is assessed in thoracic CT scans acquired with either a standard helical protocol or a low-dose helical protocol by measuring pleural space and pleural thickening in the CT scans.

In particular, according to one aspect of the present invention, there is provided a novel method for assessing pleural disease, including the steps of obtaining an image including the pleural space and/or the pleural thickening, segmenting lungs in the obtained image, constructing a chest wall image from the obtained image using a lung boundary obtained in the segmenting step, identifying ribs in the chest wall image, mapping a location of the identified ribs back into the obtained image, and determining in the obtained image the extent of the pleural space and/or the pleural thickening between the identified ribs mapped back into the obtained CT image and at least one segmented lung.

According to another aspect of the present invention, there is provided a novel system implementing the method of the invention.

According to still another aspect of the present invention, there is provided a novel computer program product, included within a computer readable medium of a computer system, which upon execution causes the computer system to perform the method of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3B shows the geometry for constructing the chest wall image according to the method of FIG. 3A based on the results of automated lung segmentation;

FIG. 3C shows an exemplary chest wall image for the right hemithorax, and the relationship between the rows and columns of the chest wall image and pixels in the original image, as a result of the method of FIG. 3A;

FIG. 8 shows an exemplary computerized pleural space measurement output according to the present invention;

DETAILED DESCRIPTION OF THE PREFERRED EMBODIMENTS

Figure 1:
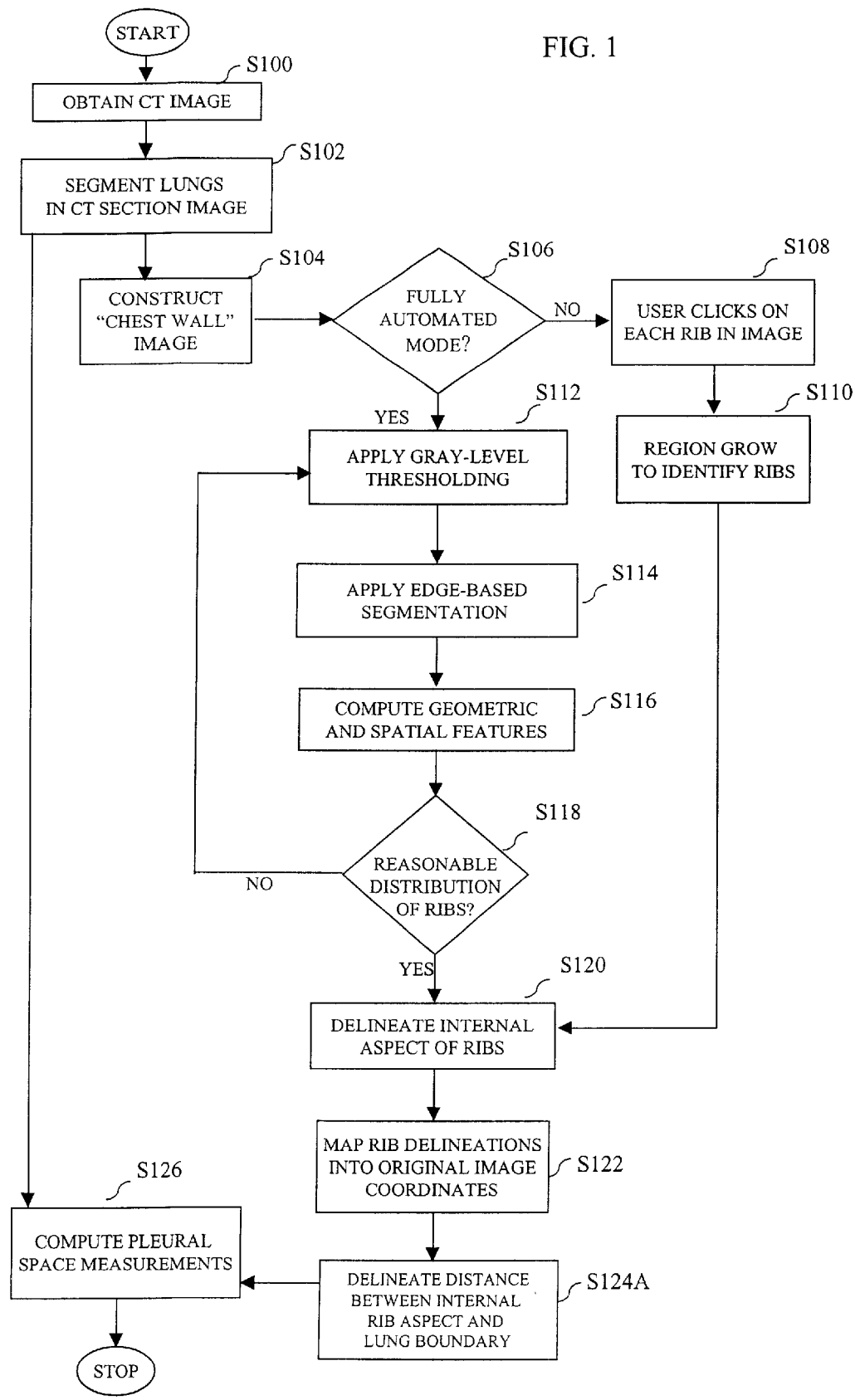
FIG. 1 is a flowchart of a first embodiment according to the present invention, illustrating a method for the delineation of the chest wall and for the measurement of pleural space and/or pleural thickening in thoracic CT scans based on a distance between lung boundary and chest wall.

Referring now to the drawings, wherein like reference numerals designate identical or corresponding parts throughout the several views FIG. 1 is a flowchart of a method for the measurement of the pleural space and/or the pleural thickening in thoracic CT scans. The overall scheme includes an initial acquisition of CT image data in step S100. For each section image, gray-level thresholding techniques are used to segment the lungs in step S102 (to be described later). A segmented lung region and its boundary serve two purposes: (1) the center-of-mass (centroid) of the segmented lung region and the set of lung boundary pixels obtained from the segmented lung region are used to construct a "chest wall image," in step S104 (to be described later), in which rib segmentation is performed, and (2) the lung boundary is combined with the delineated chest wall, which is based on rib segmentation, to provide pleural space measurements in step S126 (to be described later). The pleural space measurements include pleural space and pleural thickening.

Next, rib segmentation is performed by either of two modes: (1) semi-automated mode and (2) fully automated mode. After the chest wall image is constructed in step S104, an inquiry is made in step S106 as to whether the semi-automated or fully automated mode will be used.

If the semi-automated mode is used, the user is shown a CT section image through a graphical user interface. The basic function of such an interface is to provide a "window" that allows a radiologist or clinician to view all the images of a complete CT scan. The interface has a pull-down list from which the user selects the CT scan of interest. Buttons and slider bars allow the user to raster through the individual CT section images, adjust the contrast and brightness of the images, and zoom in on specific regions. The next layer of functionality facilitates user interaction in the semi-automated method for pleural disease assessment. In this mode, the interface prompts the user to position the mouse-driven cursor over a rib.

Since an internal aspect of a rib (i.e., the boundary of each rib closest to the lung boundary, where the lung boundary is represented by the bottom row of the chest wall image) is used to represent the chest wall, in step S108, the user manually selects a rib by a single mouse click. This manual selection may be implemented in at least the following ways. The user may select (i.e., click on) a point that lies along the internal aspect of the rib. Or the user may select any point within a rib. The selected point, the "seed point," is mapped into the chest wall image, and a gray-level-based region-growing operation is performed in step S110 to identify the complete rib as it appears in the chest wall image. Region growing identifies all pixels within a local neighborhood of the manually selected seed point that contain gray levels within a certain range of the gray level of the seed point, thus achieving rib segmentation through a semi-automated technique that requires minimal manual input. The result is a "segmented rib."

If the fully automated mode is used, image processing techniques are applied to the chest wall image to segment ribs. A gray-level threshold is applied to the chest wall image in step S112 so that only the brightest structures (i.e., the bones) in the chest wall image remain. The appropriate gray-level threshold is selected dynamically based on the distribution of gray-level values in the particular chest wall image. Edge-based segmentation methods such as a Sobel filter or a Laplacian operator (see Reference 12) are used in step S114 to complement the degree of rib segmentation achieved with gray-level-thresholding. Geometric characteristics such as eccentricity, circularity, and major axis orientation along with spatial characteristics such as distance from the lung boundary and distribution along the lung boundary are calculated in step S116 and used in step S118 to more definitively identify ribs and exclude other anatomic structures that may also satisfy the gray-level threshold and edge-based methods, thereby ensuring that all the ribs, and only the ribs, are identified in the thresholded chest wall image. For example, to eliminate non-rib structures from the chest wall image, a size criterion may be used to eliminate the small portions of scapula that remain in the thresholded chest wall image. In addition, a distance-from-the-lung-boundary parameter (i.e., a distance-from-the-bottom-of-the-image parameter) is implemented to prevent the entire scapula from being incorrectly identified as a rib. In addition, in step S118, to ensure that all ribs are segmented, the chest wall image is horizontally partitioned into compartments. Based on the observation that ribs tend to be roughly equally spaced in the chest wall image, the presence of an identified rib in each compartment is determined. If a compartment does not contain a portion of what is determined to be a rib, a less-strict gray-level threshold is applied to the pixels within that compartment. This process of lowering the gray-level threshold is repeated iteratively beginning with step S112 until a rib is identified or until some predetermined number of iterations has been reached, in which case it is determined that the compartment does not contain a rib.

After the ribs are segmented by either the semi-automated or the fully automated mode, the internal aspect of the segmented ribs is delineated in step S120. That is, a pixel along the internal aspect of the segmented rib and centered between the ends of the rib is automatically identified. This pixel is mapped to a corresponding pixel in the original CT image in step S122, where the corresponding pixel becomes the pixel upon which pleural space measurements are made. (See FIG. 6 and rib boundary pixels 610.)

Next, a line between each internal rib aspect and the lung boundary is displayed in step S124A, where the length of the line (or linear distance) indicates the pleural thickness at that position. The linear distance is measured in step S126 based on a rib pixel along the internal aspect of each rib using the lung segmentation result of step S102 superimposed with the rib segmentation result of step S124A. A linear measurement is made automatically between the rib pixel and the lung boundary to replicate the mesothelioma measurement method currently used by radiologists. (See FIG. 7 and linear lines 710.) Several variations on this distance measurement are possible. All variations involve the length of a line extending from the rib pixel to the lung boundary. First, the length of a line extending from the rib pixel to that lung boundary pixel closest to the rib pixel may be used to represent the pleural space measurement at that rib position. Second, the length of a line extending from the rib pixel to intersect the lung boundary perpendicularly may be used to represent the pleural space measurement. Third, the length of a line extending perpendicular to the internal aspect of the rib from the rib pixel to the lung boundary may be used. Different ones of these metrics may be applicable under different lung boundary/chest wall spatial relationships. The numeric data may then be presented in tabular form on a level-by-level basis at individual rib positions or as an average of all rib positions selected in a given hemithorax at one level in step S126. (See FIG. 8.)

In the semi-automated mode, if the line between the internal rib aspect and the lung boundary does not, in the opinion of the user, represent an accurate estimation of the pleural thickness at that position, the user may manually draw a line with the graphical user interface to override the semi-automated measurement. When the user has completed a scan, a report of pleural space measurements is generated.

Figure 2A:
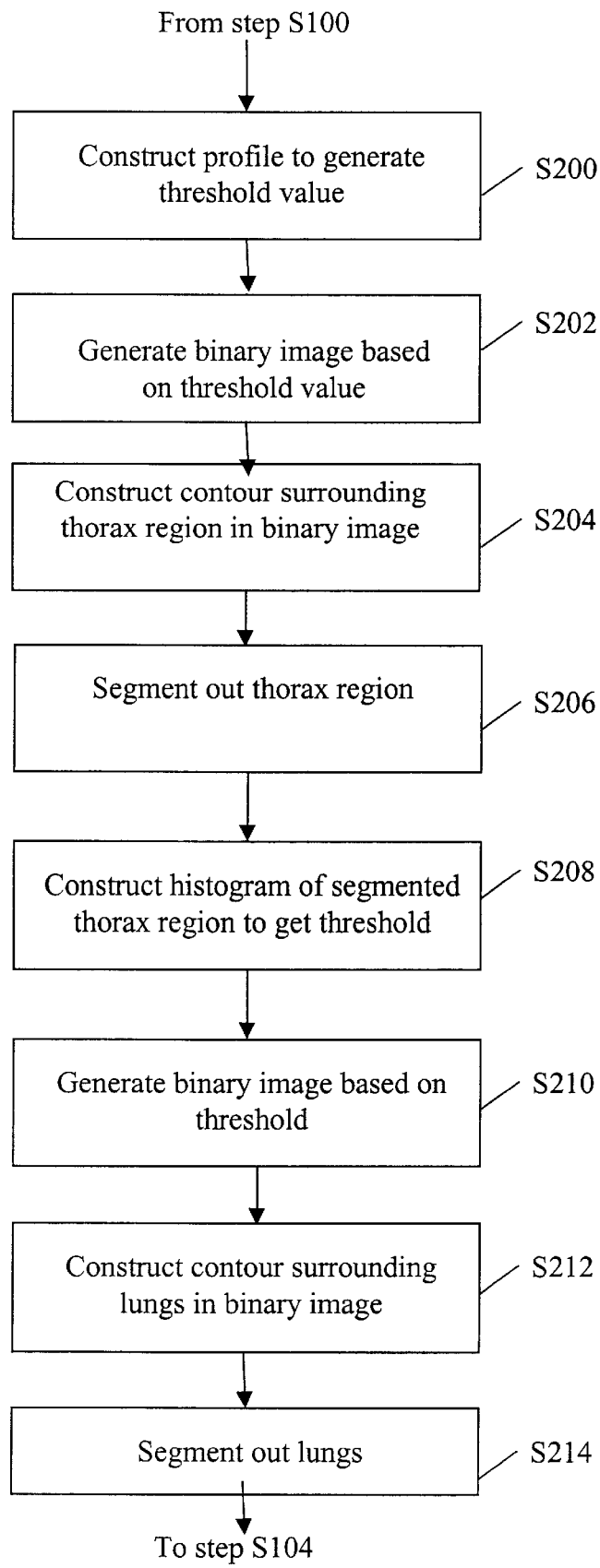
FIG. 2A is a flowchart of an automated lung segmentation method as shown in FIG. 1 according to the present invention.

FIG. 2A is a flowchart of the automated lung segmentation of step S102 in FIG. 1. To segment the lungs, the thorax is first segmented by constructing a cumulative gray-level profile from the values of pixels that lie along the diagonal that extends from a corner of the image to the image center, where the shape of this profile is analyzed to identify a single gray level as a threshold value in step S200 (see Reference 11). In step S202, a binary image is created by thresholding the section image such that a pixel is turned "on" in the binary image if the value of the corresponding pixel in the section image has a value greater than the gray-level threshold; all other pixels remain "off" in the binary image.

An eight-point contour detection scheme (see Reference 12) is used in step S204 to construct a contour surrounding the outermost boundary of the largest "on" region in the binary image (i.e., the thorax). The set of pixels in the section image that lie within this contour defines the segmented thorax region and is used to create a thorax segmentation image such that pixels within the segmented thorax region maintain their original value, in step S206. In addition, in step S206, pixels not included within the segmented thorax region are assigned a value of 0. Pixels that represent portions of the examination table that may be included within the segmented thorax region are identified and eliminated. And, the trachea and main bronchi are segmented based on a region-growing technique (see Reference 12) and eliminated from the segmented thorax region.

After the thorax region is segmented, initial lung segmentation begins for a particular section by constructing a gray-level histogram in step S208 from the pixels that lie within the segmented thorax region (see References 11, 13). The distribution of pixels in this typically bimodal histogram is used to identify a single gray level as a threshold value within the broad minimum in the histogram (see Reference 11). In step S210, a binary image is created by thresholding the thorax segmentation image such that a pixel is turned "on" in the binary image if the value of the corresponding pixel in the thorax segmentation image has a value less than the gray-level threshold; all other pixels remain "off" in the binary image. The presence of a single "on" region that spans both sides of the resulting binary image indicates that gray-level thresholding has "fused" the two lungs and that an anterior junction line is present in the section image. This anterior junction line is automatically delineated as part of step S210 based on the location of a "cleft point" in the binary image and local maximum gray-level information. Pixels along the anterior junction line are turned "off" to ensure the segmentation of two distinct lung regions.

In step S212, an eight-point contour detection scheme (see Reference 12) is used to construct contours surrounding the outermost boundaries of the two largest "on" regions in the binary image (i.e., the lungs). The sets of pixels in the section image that lie within these contours define the segmented lung regions and are used to create a lung segmentation image such that pixels within the segmented lung regions maintain their original value, in step S214. In addition, in step S214, pixels not included within the segmented lung regions are assigned a value of 0. A rolling ball algorithm (see References 14, 15) is applied to rectify the erroneous exclusion of dense structures such as juxta-pleural nodules and hilar vessels. And, to prevent pixels that belong to the diaphragm from contributing to the segmented lung regions, diaphragm analysis is performed both on the initial binary images created from gray-level thresholding and in conjunction with the rolling ball technique.

Figure 2B:
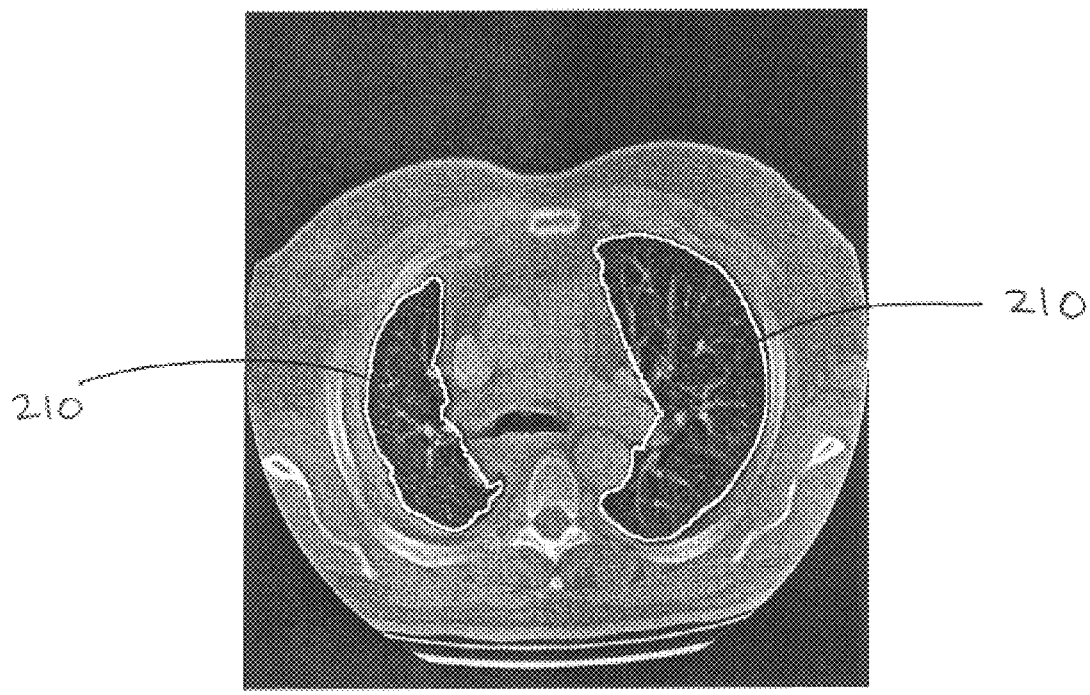
FIG. 2B shows the boundaries of the automatically extracted segmented lung regions as a result of the method of FIG. 2A superimposed on the original section image with mesothelioma in the right hemithorax.

FIG. 2B shows an exemplary result of automated lung segmentation for one CT section image demonstrating mesothelioma in the right hemithorax. The contours 210 superimposed on the original CT image represent the outermost boundaries of the segmented lung regions. These computer-determined lung boundaries provide the basis for many of the subsequent analyses.

With the lung regions segmented as described in FIG. 2A and the lung boundaries identified as the perimeters of the segmented lung regions, rib segmentation is performed next to estimate the position of the chest wall beginning with construction of the chest wall image.

Figure 3A:
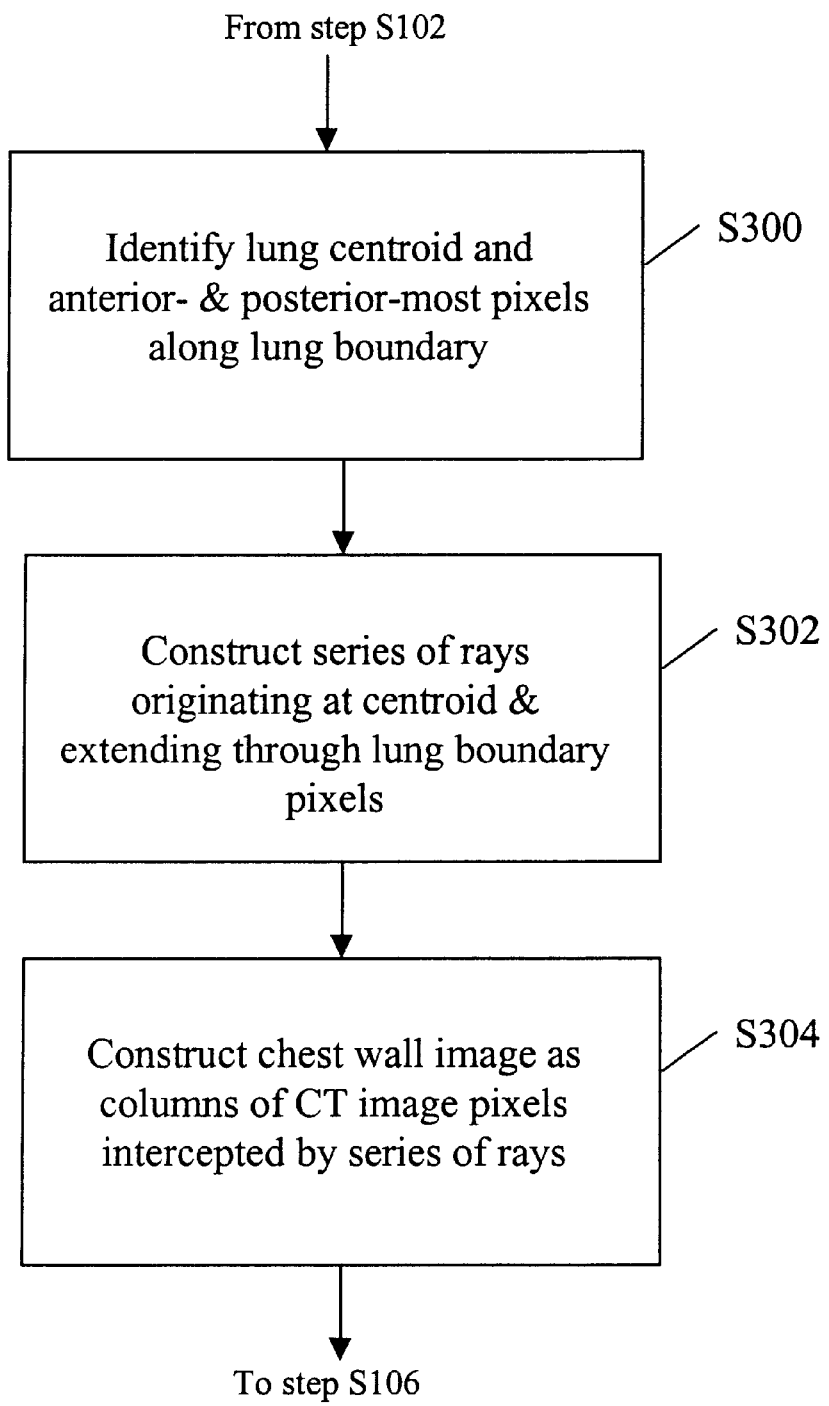
FIG. 3A is a flowchart of a method to construct a chest wall image as shown in FIG. 1 according to the present invention.

FIG. 3A is a flowchart of the chest wall image construction of step S104 of FIG. 1. FIGS. 3B and 3C show exemplary results of the chest wall image construction of FIG. 3A. In step S300 of FIG. 3A, the center-of-mass (centroid) of a lung (indicated by an "x" 310 in FIG. 3B) is identified based on the automated lung segmentation of FIG. 2A, and the anterior-most (i.e., uppermost) and posterior-most (i.e., lowermost) pixels along the lung boundary 313 are identified (indicated by the vertical hash marks 312 and 311, respectively, in FIG. 3B). Next, a series of rays is constructed originating at the lung center-of-mass and extending through each pixel along the lung boundary in step S302. Three such (non-adjacent) rays 314 are depicted in FIG. 3B.

Figures 4A, 4B:
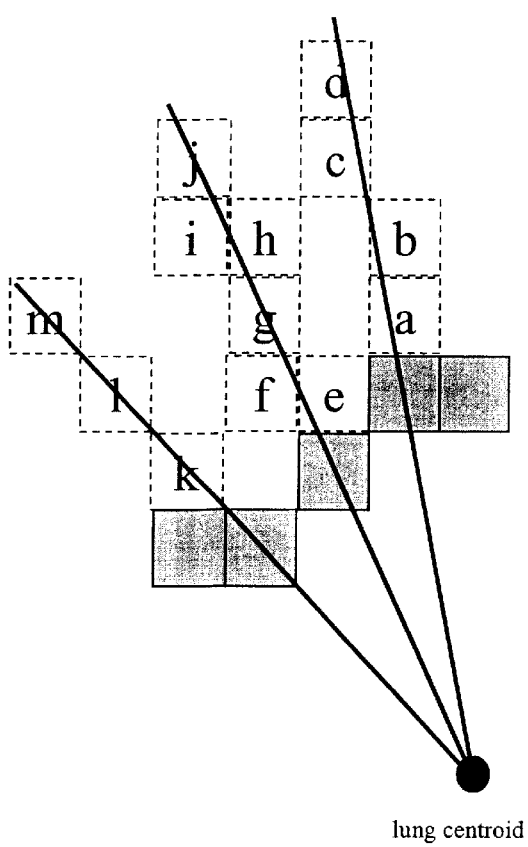
FIG. 4A is an exemplary illustration of the construction of the chest wall image based on the lung centroid (obtained from automated lung segmentation), the lung boundary (obtained from automated lung segmentation), and rays drawn from the lung centroid through individual lung boundary pixels in a CT image.
FIG. 4B illustrates the corresponding chest wall image resulting from the CT image of FIG. 4A.

The CT image pixels that are intercepted by a ray contribute to one column of the chest wall image, as shown schematically in FIGS. 4A and 4B. Therefore, since one ray is constructed through each lung boundary pixel (i.e. the gray pixels in FIG. 4A) that exists between the anterior-most and posterior-most lung pixels, the chest wall image is constructed in step S304 of FIG. 3A to include a number of columns equal to the number of corresponding lung boundary pixels. Of the CT image pixels, only intercepted CT image pixels that are beyond (i.e. outside of) the lung boundary contribute to the chest wall image (FIG. 4B). Accordingly, the first row of the chest wall image represents the CT image pixels at the lung boundary, while subsequently higher rows in the chest wall image represent progressively more peripheral pixels as shown in FIG. 3C. Alternatively, the first row of the chest wall image may represent the lung boundary pixels, the second row may represent the CT image pixels at the lung boundary, and subsequent rows may represent progressively more peripheral pixels. Thus, the chest wall image effectively provides a representation of extrapulmonary anatomy "unwrapped" about the lung boundary as shown in FIG. 3C. It should be noted that the chest wall image does not capture extrapulmonary anatomy along the mediastinal aspect of the lung boundary, although a "mediastinum image" may be constructed in a similar manner.

Figure 5A:
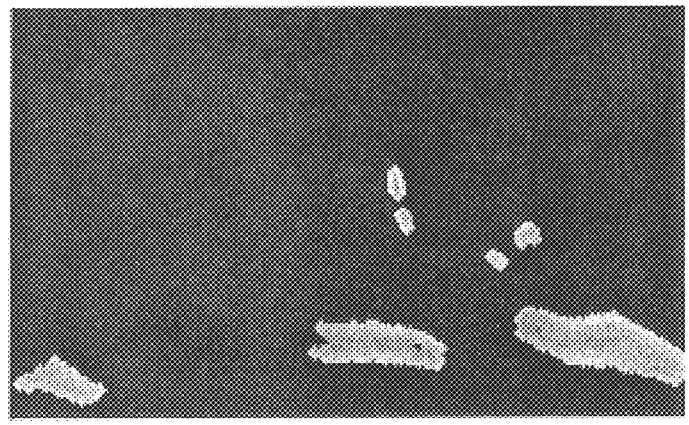
FIG. 5A shows a gray-level thresholded chest wall image indicating how the ribs may be segmented from surrounding anatomy according to the present invention.
Figure 5B:
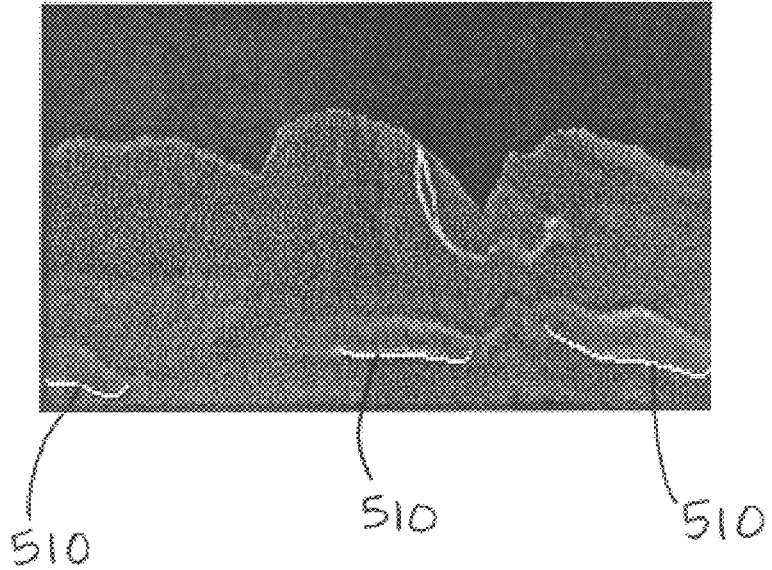
FIG. 5B shows the internal aspects of the ribs as identified from the regions in FIG. 5A superimposed on the original chest wall image of FIG. 3C.

FIG. 5A shows an exemplary rib segmentation in which only the ribs are displayed in the chest wall image according to the method described in FIG. 1. FIG. 5B shows an exemplary delineation of the segmented ribs in FIG. 5A, where the delineated pixels 510 represent the rib boundary pixels closest to the lung boundary as described in step S120 of FIG. 1. The internal aspect of each rib is delineated by selecting the single "on" pixel in each column that is closest to the bottom of the chest wall image.

Figure 6:
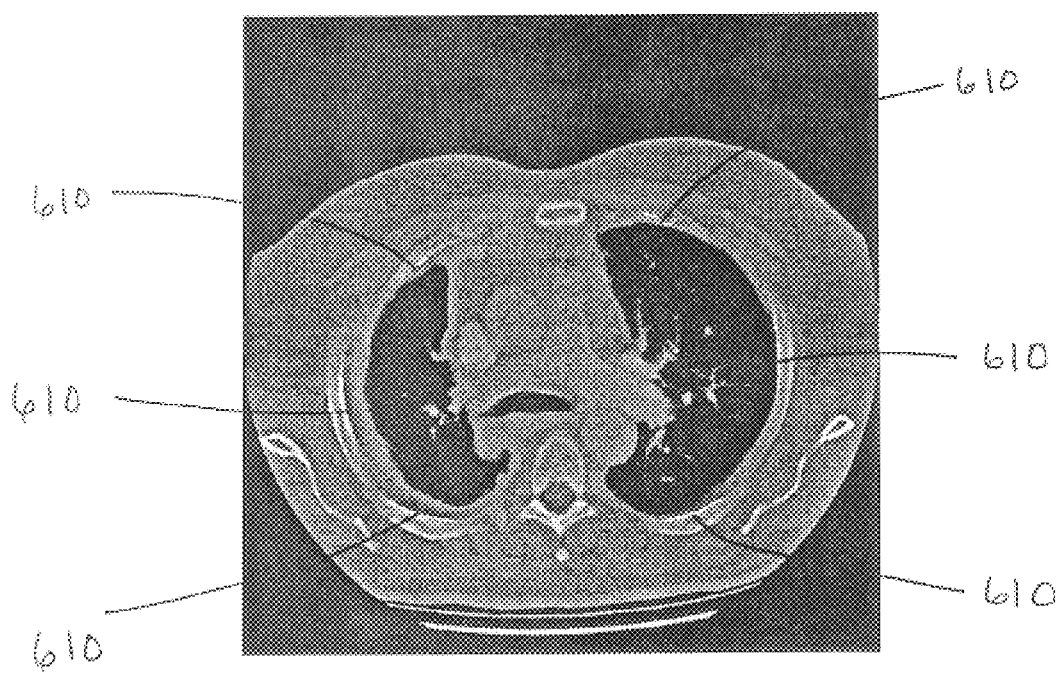
FIG. 6 demonstrates the mapping of internal rib aspect points back into original image coordinates so that the internal aspects of the ribs are now delineated in the original CT image.

FIG. 6 shows exemplary rib boundary pixels 610 that are mapped from the chest wall image back into the coordinate system of the original CT image as described in step S122 of FIG. 1. This method of rib segmentation for the purpose of automatically obtaining the internal aspects of the ribs shown in FIG. 6 has been developed based on a database of CT scans from mesothelioma patients.

Figure 7:
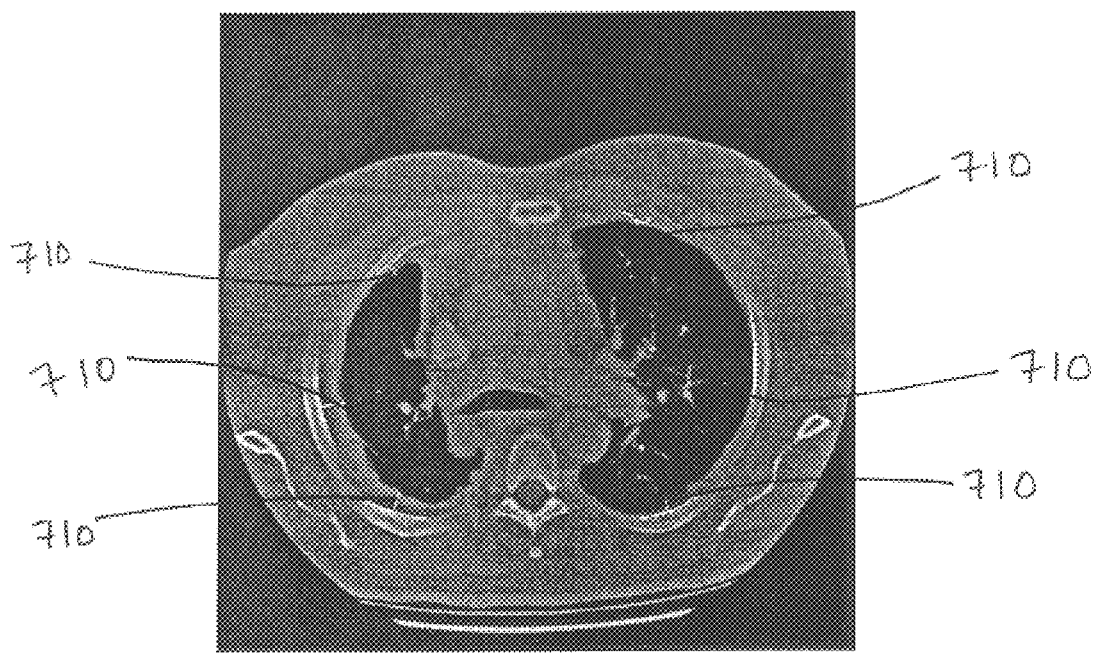
FIG. 7 shows the internal aspects of the ribs with lines extending perpendicularly from the middle point of each rib delineation to the lung boundary indicating a distance metric to measure pleural space and/or pleural thickening according to the present invention.

FIG. 7 shows exemplary lengths of lines 710 extending perpendicular to the internal aspect of the rib from the middle rib pixel of the internal aspect delineation to the lung boundary as described in step S124A of FIG. 1. As previously discussed, different ones of these line metrics may be applicable under different lung boundary/chest wall spatial relationships.

FIG. 8 shows exemplary results of the pleural space measurements of step S126 in FIG. 1 in tabular form on a level-by-level basis at individual rib positions or as an average of all rib positions selected in a given hemithorax at one level. The pleural thickness data correspond to the lengths of the perpendicular lines 710 of FIG. 7. Note that the pleural thicknesses computed for the diseased right hemithorax are substantially greater than the pleural thicknesses computed for the normal left hemithorax.

Figure 9A:
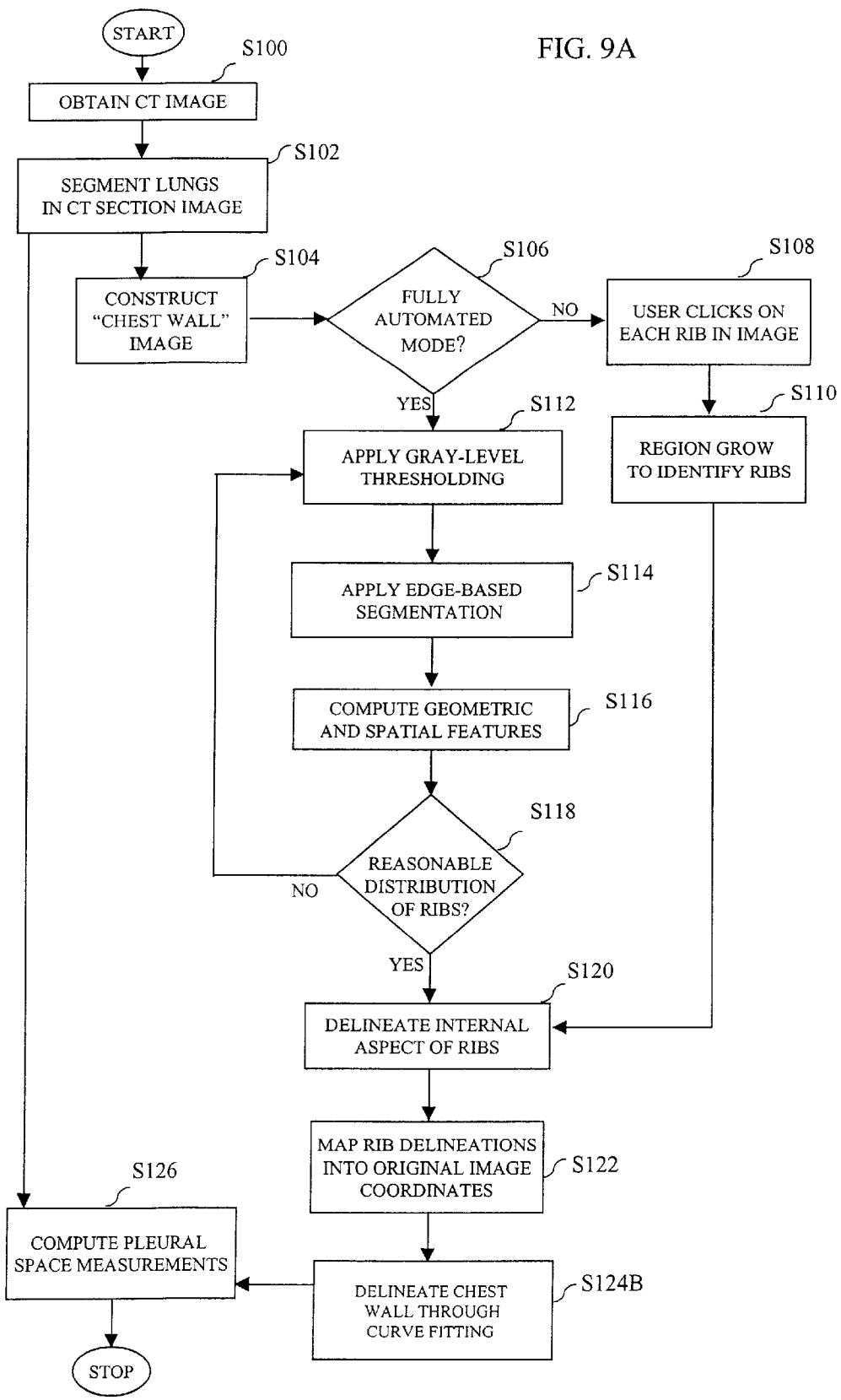
FIG. 9A is a flowchart of a second embodiment according to the present invention in which the pleural space and/or the pleural thickening is measured based on a geometric area between lung boundary and chest wall.

FIG. 9A shows another embodiment of the present invention, in which the pleural space measurement is based on the area of the pleural space and/or the pleural thickening between the anterior-most and posterior-most pixels of the lung. The steps of FIG. 9A are the same as the steps of FIG. 1 with the exceptions that step S124B replaces step 124A and step S126 performs different computations for pleural space measurement. In step S124B, the chest wall is delineated by using curve-fitting (e.g., polynomials or ellipses (see Reference 16)) or interpolation (e.g., cubic splines (see Reference 17)) based on the points along the internal aspects of the ribs in a hemithorax, from which a quantification of the area between the lung boundary and the chest wall delineation can be made. To compute the area of the pleural space and/or the pleural thickening in step S126, the number of pixels between the lung boundary and the chest wall is determined, and a conversion from number of pixels to area (in mm²) is performed.

Figure 9B:
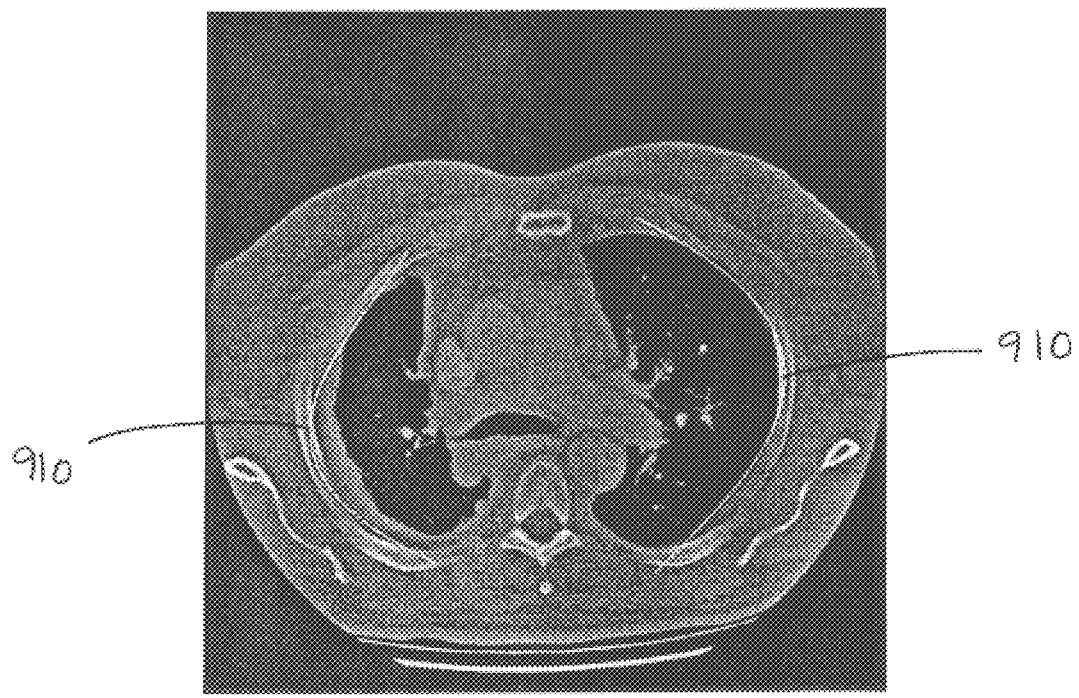
FIG. 9B illustrates how a curve-fitting technique, according to the method of FIG. 9A, applied to the internal rib aspect pixels in the right and left hemithoraces is used to delineate the right and left chest wall, respectively.
Figure 9C:
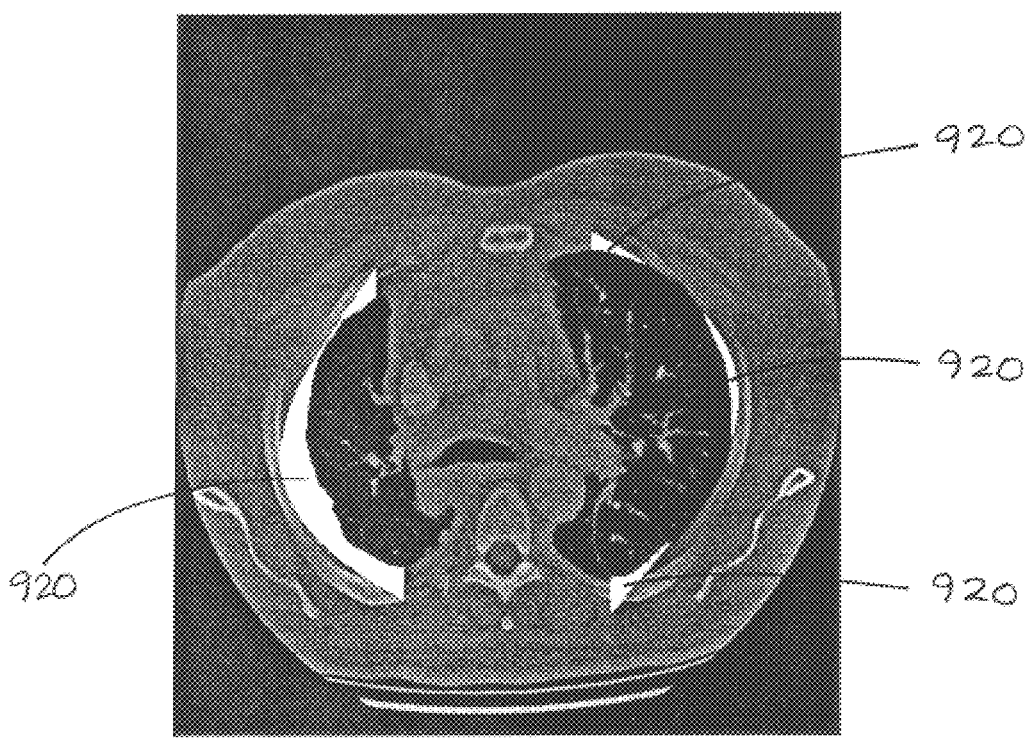
FIG. 9C shows the pixels determined to exist within the pleural space and/or the pleural thickening based on the lung boundary and the chest wall delineation, i.e., the geometric area associated with the pleural space and/or the pleural thickening computed based on these pleural-space pixels, according to the method of FIG. 9A.

FIG. 9B shows an exemplary result of the chest wall delineation 910 of step S124B in FIG. 9A. FIG. 9C shows the pixels 920 between the lung boundary and the chest wall delineation, i.e., the pixels within the pleural space and/or pleural thickening as determined in step S126. A comparison between the pleural-space area of the two hemithoraces in a CT section is then possible to assess the presence or absence of pleural disease.

Figure 10:
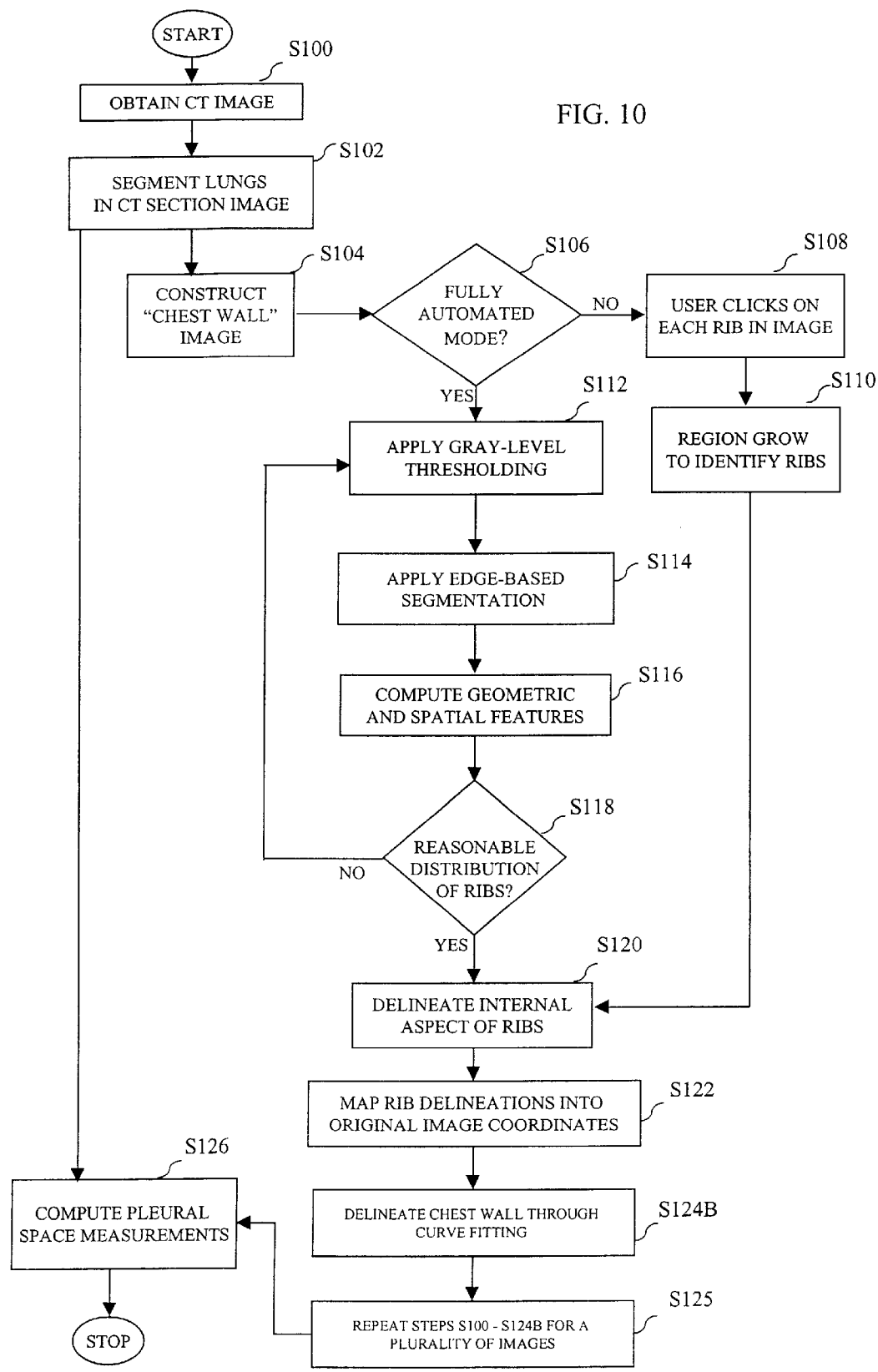
FIG. 10 is a flowchart of a third embodiment according to the present invention in which the pleural space and/or the pleural thickening is measured based on a geometric volume between lung boundary and chest wall.

FIG. 10 is a flowchart of still another embodiment of the present invention in which the complete volume of the pleural space and/or the pleural thickening is calculated. The steps of FIG. 10 are the same as the steps of FIG. 1 with the exceptions that step S124B replaces step 124A and step S126 performs different computations for the pleural space measurement. In step S124B, as in FIG. 9A, the chest wall is delineated by using curve-fitting (e.g., polynomials or ellipses (see Reference 16)) or interpolation (e.g., cubic splines (see Reference 17)) based on the points along the internal aspects of the ribs in a hemithorax, from which a quantification of the area between the lung boundary and the chest wall delineation can be made. Steps S100 through S124B are repeated for each of a plurality of CT images, as stated in step S125. After the chest wall is delineated in each of the CT images, then, in step S126, the pleural space measurement for each of the CT images is computed as an area similar to that calculated in FIG. 9A. Then, the complete volume of the two hemithoraces is computed based on an integration of all measurements made, i.e. the areas, within the sections of the entire plurality of CT images. These measurements may be used to calculate the pleural space measurement in step S126 and to quantify the extent of disease in a particular case as additional information to be incorporated into a radiologist's decision-making process, or the measurements may be used as part of a computer-aided diagnosis process that alerts radiologists of the potential for pleura-based disease in the case.

It is to be understood that the linear distance, area, and volume parameters of FIGS. 1, 9A, and 10, respectively, may be used individually or in combination to compute the pleural space measurements of the present invention.

The method of the present invention demonstrates promising performance in its ability to accurately segment the lungs, delineate the chest wall based on rib segmentation, and quantify the pleural space and/or the pleural thickening in CT scans. The invention allows radiologists to procure many measurements of a patient's mesothelioma with minimal effort. With the semi-automated technique, the distance between any number of ribs and the corresponding lung in any number of CT sections can be calculated quickly and efficiently. In addition, the fully automated technique for the quantitative evaluation of mesothelioma, without user interaction, identifies the lung boundary, identifies the chest wall border as represented by the ribs, and provides measures of the distance between the two borders as an assessment of the pleural-space thickening associated with mesothelioma. Such tools are expected to greatly enhance the utility of CT scans in the management of mesothelioma patients.

Other diseases also manifest in the pleural space, most notably pleural effusions, diffuse pleural thickening, pleural plaques, empyema, and pleural metastasis (see Reference 10). Consequently, the present invention is applicable to the evaluation of a wide range of pathologies that increase the size of the pleural space (i.e., the region between the visceral and parietal pleural, which, in the absence of disease, are in direct contact with each other) or cause pleural thickening.

Furthermore, this automated method for measuring the pleural space and/or the pleural thickening has application as part of an ensemble of computer-aided diagnostic methods that may be applied to thoracic CT scans. In addition to techniques designed to evaluate CT scans for the presence of lung nodules, emphysema, and pulmonary embolus, for example, this technique for measuring the pleural space could indicate to a radiologist the potential presence of pleura-based disease in one or both of the patient's hemithoraces. The method could compare the pleural space measures of the two hemithoraces in a scan to determine the likelihood of the presence of pleura-based disease. Alternatively, the method could be trained on a large number of normal scans to develop a statistical model of pleural-space measurements in the absence of disease and use this model to calculate the likelihood of disease in novel cases.

Figure 11:
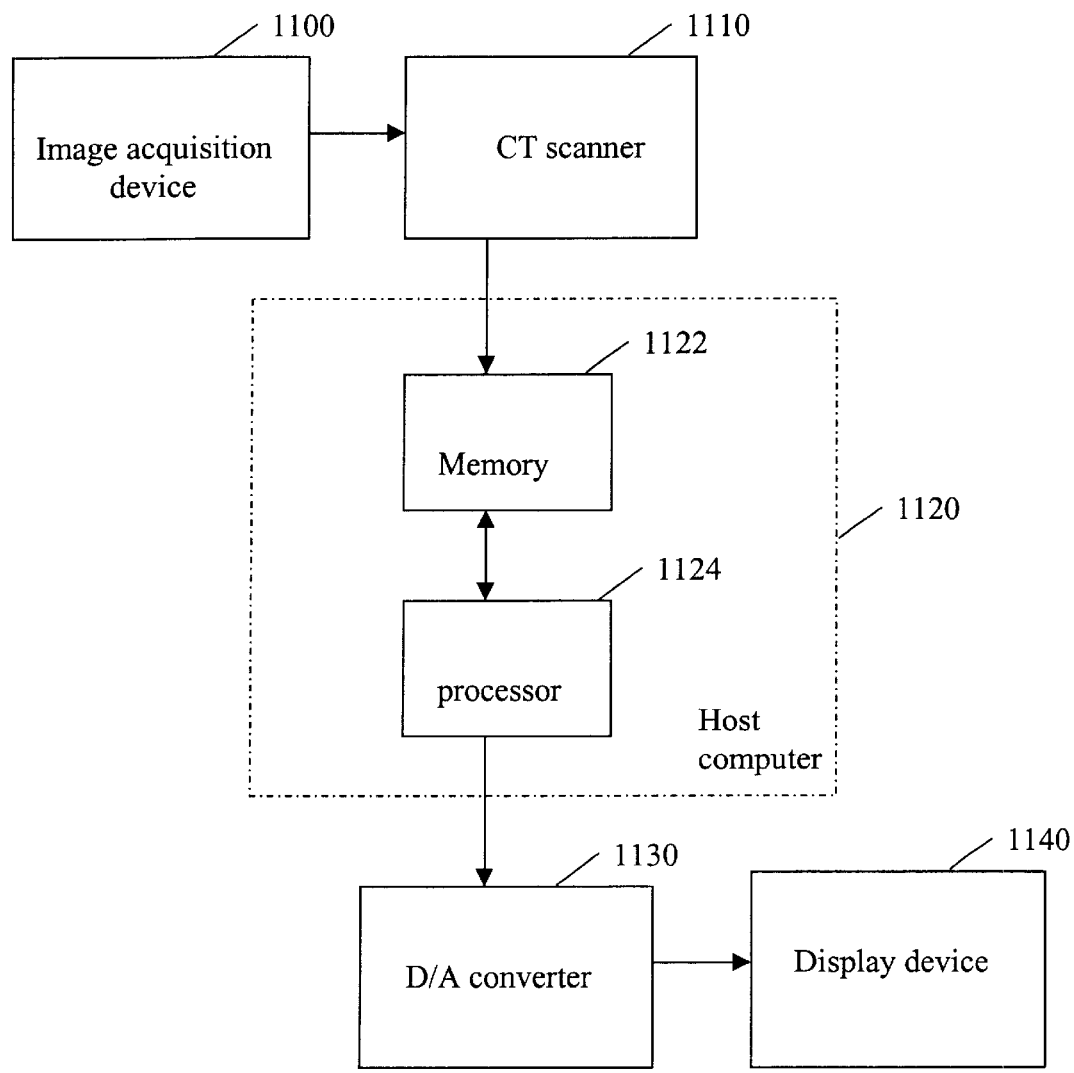
FIG. 11 is a block diagram illustrating a system implementing the present invention for the automated measurement of the pleural space and/or the pleural thickening in thoracic CT scans.

FIG. 11 shows an exemplary system used to implement the embodiments of the present invention. In FIG. 11, CT images of an object are obtained from an image acquisition device 1100 followed by a CT scanner 1110. The CT images from the CT scanner 1110 are input to a host computer 1120. Alternatively, the image data may be retrieved from an existing database via PACS (Picture Archiving Communication System). In the host computer 1120, each CT image is put into memory 1122. Upon processing to find the pleural space measurement from the CT images, the CT image data is passed to a processor 1124 where the lungs are segmented out according to the steps of FIG. 2A, the ribs are then segmented out by constructing a chest wall image according to the steps of FIG. 3A and using either the semi-automated or fully automated mode, and the lung and rib segmentation results are used to calculate the pleural space measurements which are either superimposed onto images, stored in file format, or given in text format. The results are then displayed on the display device 1140 after passing through a digital-to-analog converter 1130.

This invention conveniently may be implemented using a conventional general purpose computer or micro-processor programmed according to the teachings of the present invention, as will be apparent to those skilled in the computer art. Appropriate software can readily be prepared by programmers of ordinary skill based on the teachings of the present disclosure, as will be apparent to those skilled in the software art.

Figure 12:
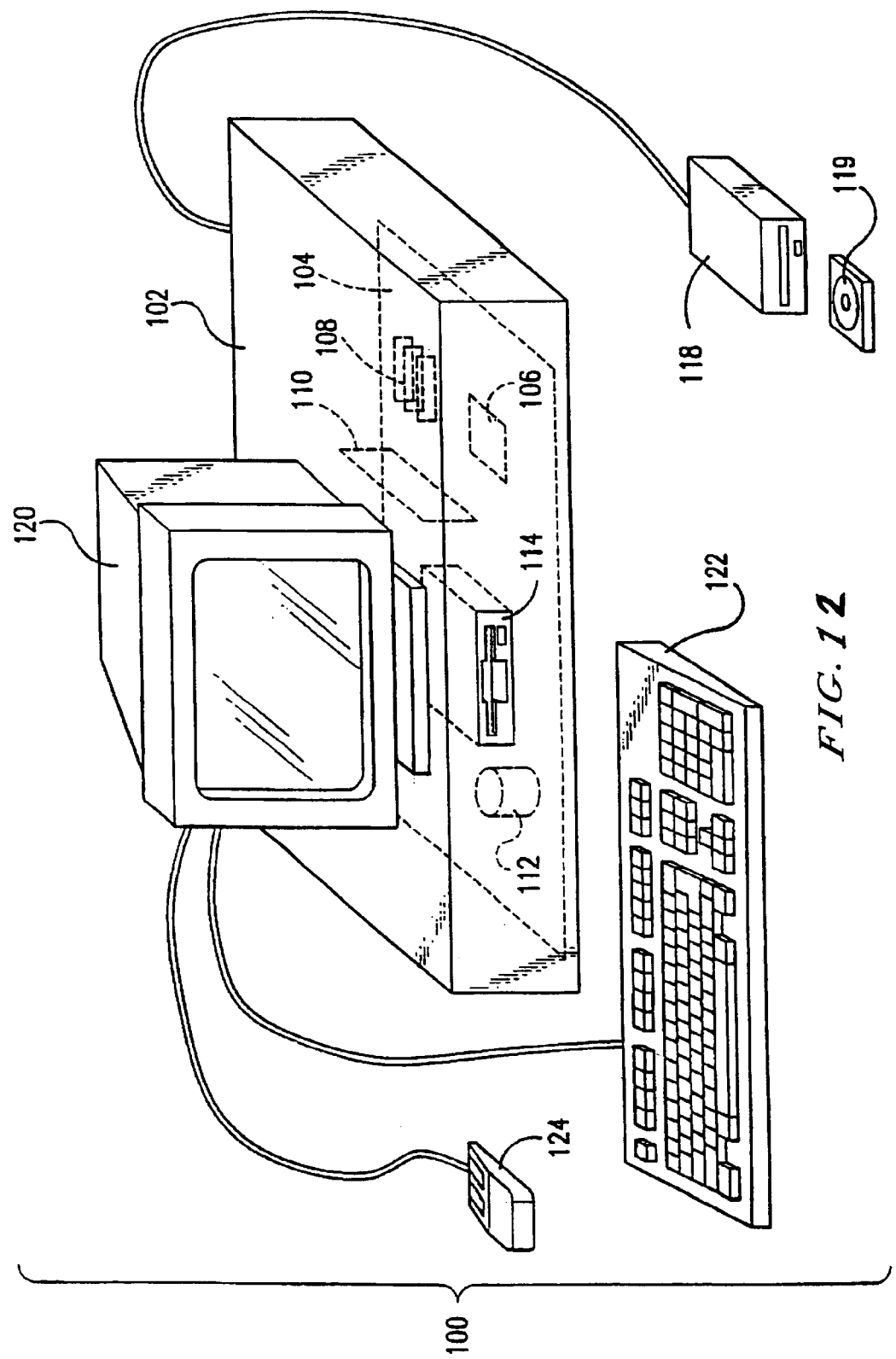
FIG. 12 is an exemplary general purpose computer programmed according to the teachings of the present invention.

FIG. 12 is a schematic illustration of a computer system for the computerized assessment of pleural disease. A computer 100 implements the method of the present invention, wherein the computer housing 102 houses a motherboard 104 which contains a CPU 106, memory 108 (e.g., DRAM, ROM, EPROM, EEPROM, SRAM, SDRAM, and Flash RAM), and other optional special purpose logic devices (e.g., ASICs) or configurable logic devices (e.g., GAL and reprogrammable FPGA). The computer 100 also includes plural input devices, (e.g., a keyboard 122 and mouse 124), and a display card 110 for controlling monitor 120. In addition, the computer 100 further includes a floppy disk drive 114; other removable media devices (e.g., compact disc 119, tape, and removable magneto-optical media (not shown)); and a hard disk 112, or other fixed, high density media drives, connected using an appropriate device bus (e.g., a SCSI bus, an Enhanced IDE bus, or a Ultra DMA bus). Also connected to the same device bus or another device bus, the computer 100 may additionally include a compact disc reader 118, a compact disc reader/writer unit (not shown) or a compact disc jukebox (not shown). Although compact disc 119 is shown in a CD caddy, the compact disc 119 can be inserted directly into CD-ROM drives which do not require caddies.

As stated above, the system includes at least one computer readable medium. Examples of computer readable media are compact discs 119, hard disks 112, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer 100 and for enabling the computer 100 to interact with a human user. Such software may include, but is not limited to, device drivers, operating systems and user applications, such as development tools. Such computer readable media further includes the computer program product of the present invention for performing the inventive method of the present invention. The computer code devices of the present invention can be any interpreted or executable code mechanism, including but not limited to scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional components circuits, as will be readily apparent to those skilled in the art.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for determining an extent of at least one of a pleural space and a pleural thickening, comprising the steps of:

obtaining an image including at least one of the pleural space and the pleural thickening;

segmenting lungs in the obtained image;

constructing a chest wall image from the obtained image through a mapping of pixels external to a lung boundary obtained in the segmenting step;

identifying ribs in the chest wall image;

mapping a location of the identified ribs back into the obtained image; and determining in the obtained image the extent of the at least one of the pleural space and the pleural thickening between the identified ribs mapped back to the obtained image and at least one segmented lung.

2. The method of claim 1, wherein the segmenting step comprises:

constructing a gray-level profile of the obtained image from which a first threshold value is generated;

generating a first binary image of the obtained image based on the first threshold value;

constructing a first contour surrounding a region in the first binary image;

identifying pixels within the first contour to produce a segmented thorax image;

constructing a gray-level histogram of the segmented thorax image from which a second threshold value is generated;

generating a second binary image of the segmented thorax image based on the second threshold value;

constructing second contours surrounding regions in the second binary image; and identifying pixels within the second contours as the segmented lungs.

3. The method of claim 1, wherein the constructing step comprises:

identifying a centroid of the at least one segmented lung;

identifying anterior- and posterior-most pixels along the lung boundary of the at least one segmented lung;

constructing a series of rays originating at the centroid and extending through the lung boundary; and constructing the chest wall image as columns of pixels intercepted by the series of rays.

4. The method of claim 3, wherein the step of constructing the series of rays comprises:

constructing a respective ray intercepting each pixel along the lung boundary between the anterior- and posterior-most pixels.

5. The method of claim 1, wherein the identifying step comprises:

manually selecting a point on a rib in the obtained image;

mapping the manually selected point into the chest wall image; and region-growing the mapped, manually selected point in the chest wall image to identify the rib.

6. The method of claim 5, wherein the manually selecting step comprises:

selecting the point that lies along a rib boundary closest to the lung boundary.

7. The method of claim 5, wherein the manually selecting step comprises:

selecting the point that lies anywhere on the rib.

8. The method of claim 1, wherein the identifying step comprises:

applying gray-level thresholding to the chest wall image based on a gray-level threshold value to identify regions in the chest wall image;

applying edge-based segmentation to an image resulting from the step of applying gray-level thresholding;

determining geometric and spatial features of an image resulting from the step of applying edge-based segmentation; and analyzing the geometric and spatial features to determine if the features represent a predetermined distribution of the ribs in the regions, wherein if the features do not represent the predetermined distribution of the ribs, the gray-level threshold value is lowered and the steps of applying gray-level thresholding, applying edge-based segmentation, determining geometric and spatial features, and analyzing are repeated.

9. The method of claim 8, wherein the step of determining geometric and spatial features comprises:

determining the geometric features including eccentricity, circularity, and major axis orientation; and determining the spatial features including distance of the regions from the lung boundary, size of the regions, and distribution of the regions along the lung boundary.

10. The method of claim 1, wherein the determining step comprises:

determining a distance between the identified ribs mapped back into the obtained image and the at least one segmented lung in the obtained image.

11. The method of claim 1, wherein the determining step comprises:

determining a distance between the identified ribs mapped back into the obtained image and the lung boundary closest to the identified ribs in the obtained image.

12. The method of claim 1, wherein the determining step comprises:

determining a distance between the identified ribs mapped back into the obtained image and the at least one segmented lung in the obtained image, wherein the distance corresponds to a length of a line extending from a pixel of the identified ribs and intersecting the lung boundary perpendicularly.

13. The method of claim 1, wherein the determining step comprising:

determining a distance between the identified ribs mapped back into the obtained image and the at least one segmented lung in the obtained image, wherein the distance corresponds to a length of a line perpendicular to a rib boundary of the identified ribs and extending from a pixel of the identified ribs to intersect the lung boundary.

14. The method of claim 1, wherein the determining step comprises:

manually delineating a distance between the identified ribs mapped back into the obtained image and the at least one segmented lung in the obtained image; and determining a length of the manually delineated distance.

15. The method of claim 1, wherein the determining step comprises:

determining a chest wall in the obtained image based on the location of the identified ribs; and determining a number of pixels between the determined chest wall and the at least one segmented lung.

16. The method of claim 15, wherein the step of determining the extent of the at least one of the pleural space and the pleural thickening comprises:

converting the number of pixels to an area.

17. The method of claim 15, wherein the step of determining a chest wall comprises:

determining the chest wall by one of curve-fitting and interpolation.

18. The method of claim 1, wherein the determining step comprises:

a) determining a chest wall in the obtained image based on the location of the identified ribs mapped back into the obtained image;

b) determining a number of pixels between the determined chest wall and the at least one segmented lung;

c) repeating steps a) and b) for a plurality of obtained images; and d) determining a volume of the at least one of the pleural space and the pleural thickening based on the determined number of pixels between the chest wall and the at least one segmented lung in the plurality of obtained images.

19. The method of claim 18, wherein the step of determining a chest wall comprises:

determining the chest wall by one of curve-fitting and interpolation.

20. A system implementing the method of any one of claims 1 through 19.

21. A computer program product storing program instructions for execution on a computer system, which when executed by the computer system, cause the computer system to perform the method recited in any one of claims 1 through 19.

* * * * *